United States Patent
Govari et al.

(10) Patent No.: US 8,900,229 B2
(45) Date of Patent: *Dec. 2, 2014

(54) HIGH-SENSITIVITY PRESSURE-SENSING PROBE

(71) Applicant: Biosense Webster (Israel), Ltd., New Brunswick, NJ (US)

(72) Inventors: Assaf Govari, Haifa (IL); Yaron Ephrath, Kakur (IL); Ariel Garcia, Glendora, CA (US); Andres Claudio Altmann, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/971,955

(22) Filed: Aug. 21, 2013

(65) Prior Publication Data

US 2014/0024969 A1 Jan. 23, 2014

Related U.S. Application Data

(63) Continuation of application No. 12/327,226, filed on Dec. 3, 2008, now Pat. No. 8,535,308, which is a continuation-in-part of application No. 11/868,733, filed on Oct. 8, 2007, now Pat. No. 8,357,152.

(51) Int. Cl.
*A61B 18/18* (2006.01)
*A61B 5/05* (2006.01)
(Continued)

(52) U.S. Cl.
CPC . *A61B 5/48* (2013.01); *A61N 1/056* (2013.01); *A61B 2019/5251* (2013.01); *A61B 5/06*
(Continued)

(58) Field of Classification Search
CPC .... A61B 1/00158; A61B 5/062; A61B 5/065;
A61B 8/42; A61B 8/4245; A61B 8/4254;
A61B 8/4263; A61B 18/04; A61B 18/08;
A61B 18/082; A61B 18/12; A61B 18/14;
A61B 18/1477; A61B 18/1482; A61B
18/1492; A61B 18/18; A61B 2562/0223
USPC ........................... 606/27–34, 41, 45; 128/898
See application file for complete search history.

(56) References Cited

U.S. PATENT DOCUMENTS 3,841,150 A 10/1974 Pearson
3,971,364 A 7/1976 Fletcher et al.
(Continued)

FOREIGN PATENT DOCUMENTS

DE 19750441 A 6/1999
EP 928601 A1 7/1999
(Continued)

OTHER PUBLICATIONS

Biter, William J. et al., "Magnetic Wire Strain Sensor", 33rd International Sampe Technical Conference, Nov. 5-8, 2001, vol. 33, pp. 12-23, Seattle, WA.

(Continued)

*Primary Examiner* — Michael Peffley
*Assistant Examiner* — Khadijeh Vahdat

(57) ABSTRACT

A medical probe includes an insertion tube, having a longitudinal axis and having a distal end. A distal tip is disposed at the distal end of the insertion tube and is configured to be brought into contact with a body tissue. A joint couples the distal tip to the distal end of the insertion tube. A joint sensor, contained within the probe, senses a position of the distal tip relative to the distal end of the insertion tube. The joint sensor includes first and second subassemblies, which are disposed within the probe on opposite, respective sides of the joint and each include one or more magnetic transducers.

28 Claims, 2 Drawing Sheets

(51) Int. Cl.
*A61B 5/00* (2006.01)
*A61N 1/05* (2006.01)
*A61B 5/06* (2006.01)
*A61B 18/14* (2006.01)
*A61B 1/00* (2006.01)
*A61B 19/00* (2006.01)
*A61N 1/08* (2006.01)
*A61B 18/00* (2006.01)

(52) U.S. Cl.
CPC ........ (2013.01); *A61B 5/065* (2013.01); *A61B 2562/0247* (2013.01); *A61N 1/08* (2013.01); *A61B 18/1492* (2013.01); *A61B 2019/464* (2013.01); *A61B 5/6885* (2013.01); *A61B 2019/465* (2013.01); *A61B 2018/00351* (2013.01); *A61B 1/0008* (2013.01); *A61B 2019/5458* (2013.01)
USPC ............... 606/41; 600/12; 600/145; 600/424; 606/33; 606/34

(56) References Cited

U.S. PATENT DOCUMENTS

| | | | |
|---|---|---|---|
| 4,764,114 A | 8/1988 | Jeffcoat et al. | |
| 4,856,993 A | 8/1989 | Maness et al. | |
| 4,930,494 A | 6/1990 | Takehana et al. | |
| 5,263,493 A | 11/1993 | Avitall | |
| 5,368,564 A | 11/1994 | Savage | |
| 5,391,199 A | 2/1995 | Ben-Haim | |
| 5,462,527 A | 10/1995 | Stevens-Wright et al. | |
| 5,487,757 A | 1/1996 | Truckai et al. | |
| 5,499,542 A | 3/1996 | Morlan | |
| 5,542,434 A | 8/1996 | Imran et al. | |
| 5,558,091 A | 9/1996 | Acker et al. | |
| 5,563,354 A | 10/1996 | Kropp | |
| 5,662,124 A | 9/1997 | Wilk | |
| 5,673,695 A | 10/1997 | McGee et al. | |
| 5,680,860 A | 10/1997 | Imran | |
| 5,685,878 A | 11/1997 | Falwell et al. | |
| 5,728,149 A | 3/1998 | Laske et al. | |
| 5,769,843 A | 6/1998 | Abela et al. | |
| 5,826,576 A | 10/1998 | West | |
| 5,833,608 A | 11/1998 | Acker | |
| 5,836,894 A | 11/1998 | Sarvazyan | |
| 5,860,974 A | 1/1999 | Abele | |
| 5,861,024 A | 1/1999 | Rashidi | |
| 5,902,248 A | 5/1999 | Millar et al. | |
| 5,916,147 A | 6/1999 | Boury | |
| 5,944,022 A | 8/1999 | Nardella et al. | |
| 5,947,320 A | 9/1999 | Bordner et al. | |
| 5,964,757 A | 10/1999 | Ponzi | |
| 5,974,320 A | 10/1999 | Ward et al. | |
| 5,983,126 A | 11/1999 | Wittkampf | |
| 6,048,329 A | 4/2000 | Thompson et al. | |
| 6,063,022 A * | 5/2000 | Ben-Haim | 600/41 |
| 6,123,699 A | 9/2000 | Webster, Jr. | |
| 6,171,277 B1 | 1/2001 | Ponzi | |
| 6,177,792 B1 | 1/2001 | Govari et al. | |
| 6,183,463 B1 | 2/2001 | Webster, Jr. | |
| 6,198,974 B1 | 3/2001 | Webster, Jr. | |
| 6,201,387 B1 | 3/2001 | Govari | |
| 6,203,493 B1 | 3/2001 | Ben Haim | |
| 6,216,027 B1 | 4/2001 | Willis et al. | |
| 6,226,542 B1 | 5/2001 | Reisfeld | |
| 6,239,724 B1 | 5/2001 | Doron et al. | |
| 6,241,724 B1 | 6/2001 | Fleischman et al. | |
| 6,266,551 B1 | 7/2001 | Osadchy et al. | |
| 6,272,371 B1 * | 8/2001 | Shlomo | 600/424 |
| 6,272,672 B1 | 8/2001 | Conway | |
| 6,301,496 B1 | 10/2001 | Reisfeld | |
| 6,332,089 B1 | 12/2001 | Acker et al. | |
| 6,334,837 B1 | 1/2002 | Hein | |
| 6,335,617 B1 | 1/2002 | Osadchy et al. | |
| 6,351,549 B1 | 2/2002 | Souluer | |
| 6,436,059 B1 | 8/2002 | Zanelli | |
| 6,456,864 B1 | 9/2002 | Swanson et al. | |
| 6,484,118 B1 | 11/2002 | Govari | |
| 6,551,302 B1 | 4/2003 | Rosinko et al. | |
| 6,569,098 B2 | 5/2003 | Kawchuk | |
| 6,574,492 B1 | 6/2003 | Ben Haim et al. | |
| 6,584,856 B1 | 7/2003 | Biter et al. | |
| 6,602,242 B1 | 8/2003 | Fung et al. | |
| 6,612,992 B1 | 9/2003 | Hossack et al. | |
| 6,618,612 B1 | 9/2003 | Acker et al. | |
| 6,690,963 B2 * | 2/2004 | Ben-Haim et al. | 600/424 |
| 6,695,808 B2 | 2/2004 | Tom | |
| 6,711,429 B1 | 3/2004 | Gilboa et al. | |
| 6,727,371 B2 | 4/2004 | Müller et al. | |
| 6,814,733 B2 | 11/2004 | Schwartz et al. | |
| 6,835,173 B2 | 12/2004 | Couvillon, Jr. | |
| 6,892,091 B1 | 5/2005 | Ben Haim et al. | |
| 6,915,149 B2 | 7/2005 | Ben Haim | |
| 6,945,956 B2 | 9/2005 | Waldhauser et al. | |
| 6,964,205 B2 | 11/2005 | Papakostas et al. | |
| 6,973,339 B2 | 12/2005 | Govari | |
| 6,997,924 B2 | 2/2006 | Schwartz et al. | |
| 7,077,823 B2 | 7/2006 | McDaniel | |
| 7,156,816 B2 | 1/2007 | Schwartz et al. | |
| 7,235,070 B2 | 6/2007 | Vanney | |
| 7,297,116 B2 | 11/2007 | Varghese et al. | |
| 7,306,593 B2 | 12/2007 | Keidar et al. | |
| 7,306,599 B2 | 12/2007 | Karasawa et al. | |
| 7,311,704 B2 | 12/2007 | Paul et al. | |
| 7,397,364 B2 | 7/2008 | Govari | |
| 7,435,232 B2 | 10/2008 | Liebschner | |
| 7,465,288 B2 | 12/2008 | Dudney et al. | |
| 7,481,774 B2 | 1/2009 | Brockway et al. | |
| 7,536,218 B2 | 5/2009 | Govari et al. | |
| 7,604,605 B2 | 10/2009 | Zvuloni | |
| 7,662,151 B2 | 2/2010 | Crompton, Jr. et al. | |
| 7,681,432 B2 | 3/2010 | Hay et al. | |
| 7,686,767 B2 | 3/2010 | Maschke | |
| 7,914,440 B2 | 3/2011 | Otawara | |
| 7,959,601 B2 | 6/2011 | McDaniel et al. | |
| 7,984,659 B2 | 7/2011 | Fujimoto et al. | |
| 8,043,216 B2 | 10/2011 | Matsumura | |
| 8,046,049 B2 | 10/2011 | Govari et al. | |
| 8,083,691 B2 | 12/2011 | Goldenberg et al. | |
| 8,137,275 B2 | 3/2012 | Fan et al. | |
| 8,374,819 B2 | 2/2013 | Govari et al. | |
| 8,437,832 B2 * | 5/2013 | Govari et al. | 600/424 |
| 2001/0047129 A1 | 11/2001 | Hall et al. | |
| 2001/0047133 A1 | 11/2001 | Gilboa et al. | |
| 2002/0002329 A1 | 1/2002 | Avitall | |
| 2002/0065455 A1 * | 5/2002 | Ben-Haim et al. | 600/407 |
| 2002/0068866 A1 | 6/2002 | Zikorus et al. | |
| 2002/0068931 A1 | 6/2002 | Wong et al. | |
| 2002/0165461 A1 | 11/2002 | Hayzelden et al. | |
| 2002/0193781 A1 | 12/2002 | Loeb | |
| 2003/0120150 A1 | 6/2003 | Govari | |
| 2003/0120195 A1 | 6/2003 | Milo et al. | |
| 2003/0130615 A1 | 7/2003 | Tom | |
| 2003/0158494 A1 | 8/2003 | Dahl et al. | |
| 2003/0187389 A1 | 10/2003 | Morency et al. | |
| 2004/0049255 A1 | 3/2004 | Jain et al. | |
| 2004/0064024 A1 * | 4/2004 | Sommer | 600/374 |
| 2004/0068178 A1 | 4/2004 | Govari | |
| 2004/0097806 A1 | 5/2004 | Hunter et al. | |
| 2004/0102769 A1 | 5/2004 | Schwartz et al. | |
| 2004/0147920 A1 * | 7/2004 | Keidar | 606/34 |
| 2004/0244024 A1 | 12/2004 | Hajdukiewicz et al. | |
| 2004/0254458 A1 | 12/2004 | Govari | |
| 2005/0033135 A1 | 2/2005 | Govari | |
| 2005/0080429 A1 | 4/2005 | Freyman et al. | |
| 2005/0096590 A1 | 5/2005 | Gullickson et al. | |
| 2005/0228274 A1 | 10/2005 | Boese et al. | |
| 2005/0277875 A1 | 12/2005 | Selkee | |
| 2006/0009690 A1 | 1/2006 | Fuimaono et al. | |
| 2006/0009735 A1 | 1/2006 | Viswanathan et al. | |
| 2006/0015096 A1 | 1/2006 | Hauck et al. | |
| 2006/0064038 A1 | 3/2006 | Omata et al. | |
| 2006/0074297 A1 | 4/2006 | Viswanathan | |
| 2006/0173480 A1 | 8/2006 | Zhang | |

(56) References Cited

U.S. PATENT DOCUMENTS

| | | |
|---|---|---|
| 2006/0184106 A1 | 8/2006 | McDaniel et al. |
| 2006/0200049 A1 | 9/2006 | Leo et al. |
| 2006/0247618 A1 | 11/2006 | Kaplan et al. |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0106115 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167818 A1 | 7/2007 | Osborn, III et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197896 A1 | 8/2007 | Wallace et al. |
| 2007/0197927 A1 | 8/2007 | Ofek et al. |
| 2007/0197939 A1 | 8/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsummura |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1* | 4/2009 | Govari et al. ............ 606/34 |
| 2009/0138007 A1* | 5/2009 | Govari et al. ............ 606/33 |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1* | 6/2012 | Ludwin et al. ............ 600/11 |
| 2012/0149967 A1* | 6/2012 | Ludwin et al. ............ 600/11 |
| 2012/0150075 A1* | 6/2012 | Ludwin et al. ............ 600/587 |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| WO | WO 94/17856 A1 | 8/1994 |
| WO | WO 95/10326 A | 4/1995 |
| WO | WO 96/05768 A | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/029563 A | 3/2006 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 A | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |
| WO | WO 2011/046874 A1 | 4/2011 |

OTHER PUBLICATIONS

Biter, William J. et al., "Magnetic Wire for Monitoring Strain in Composites", *Sensors*, Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

(56) References Cited

OTHER PUBLICATIONS

Instron Marketing Brochure, "Medical Device Testing Systems", Instron 2007 http://web.archive.org/web/20080318092822/http://www.instron.com.tr/wa/library/streamfile.aspx?doc=1678&downland=true.
Instron, "Series 3300 Load Frames, Reference Manual Equipment", Instron, pp. 1-5 and 1-10, 2004.
Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).
Okumura, M.D. Yasuo et al. "A Systematic Analysis of In Vivo Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.
Peirs, J. et al., "Design of an Optical Force Sensor for Force Feedback during Minimally Invasive Robotic Surgery", Eurosensors XVII, 2003, pp. 1063-1066, http://mech.kuleuven.be/micro/pub/medic/Paper_Eurosensors_2003_MIS_sensor_extended.pdf.
Partial European Search Report mailed on Sep. 18, 2009 from corresponding European Patent Application No. 08253265.6.
Partial European Search Report mailed on Dec. 7, 2009 from related European Patent Application No. 09251502.2.
European Search Report mailed on Mar. 8, 2010 from related European Patent Application No. 09252143.4.
Partial European Search Report mailed on Mar. 29, 2010 from related European Patent Application No. 09252879.3.
Partial European Search Report mailed on Apr. 1, 2010 from corresponding European Patent Application No. 09252721.7.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from corresponding European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from corresponding European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

\* cited by examiner

HIGH-SENSITIVITY PRESSURE-SENSING PROBE

CROSS-REFERENCE TO RELATED APPLICATION

This application is a continuation of U.S. patent application Ser. No. 12/327,226, filed Dec. 3, 2008, now U.S. Pat. No. 8,535,308, which is a continuation-in-part of U.S. patent application Ser. No. 11/868,733, filed Oct. 8, 2007, now U.S. Pat. No. 8,357,152, which is assigned to the assignee of the present patent application and whose disclosure is incorporated herein by reference.

FIELD OF THE INVENTION

The present invention relates generally to invasive medical devices, and specifically to methods and devices for sensing displacement of a joint in a probe, such as a catheter, that is applied to the body of a patient.

BACKGROUND OF THE INVENTION

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

A number of patent publications describe catheters with integrated pressure sensors for sensing tissue contact. As one example, U.S. Patent Application Publication 2007/0100332, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

SUMMARY OF THE INVENTION

The embodiments of the present invention that are described hereinbelow provide novel apparatus and methods for sensing displacement of a joint, by generating and sensing magnetic fields using magnetic transducers, such as coils, on opposite sides of the joint. A disclosed embodiment relates specifically to the use of this sort of sensing apparatus in an invasive medical probe, in which the apparatus provides an indication of pressure exerted on the tip of the probe. The principles of the present invention, however, are similarly useful in applications of other sorts that require accurate sensing of joint displacement.

There is therefore provided, in accordance with an embodiment of the present invention a medical probe, including an insertion tube, having a longitudinal axis and having a distal end. A distal tip is disposed at the distal end of the insertion tube and is configured to be brought into contact with a body tissue. A joint couples the distal tip to the distal end of the insertion tube. A joint sensor, contained within the probe, senses a position of the distal tip relative to the distal end of the insertion tube, the joint sensor including first and second subassemblies, which are disposed within the probe on opposite, respective sides of the joint and each include one or more magnetic transducers.

In some embodiments, the magnetic transducers includes coils, and the first subassembly includes a first coil having a first coil axis parallel to the longitudinal axis of the insertion tube, and the second subassembly includes two or more second coils in different, respective radial locations within a section of the probe that is spaced apart axially from the first subassembly. In one embodiment, the second coils have respective second coil axes that are parallel to the longitudinal axis of the insertion tube. Additionally or alternatively, the two or more second coils include at least three second coils, which are disposed within an axial plane of the probe at different, respective azimuthal angles about the longitudinal axis.

In a disclosed embodiment, the joint sensor is configured to generate a signal indicative of an axial displacement and an orientation of the distal tip relative to the distal end of the insertion tube. Typically one of the first and second subassemblies is coupled to be driven by an electrical current to emit at least one magnetic field, and the other of the first and second subassemblies is coupled to output one or more signals in response to the at least one magnetic field, wherein the signals are indicative of the position of the distal tip relative to the distal end of the insertion tube.

In one embodiment, the probe includes a position sensor for sensing position coordinates of the probe relative to a frame of reference that is separate from the probe. Additionally or alternatively, the distal tip includes an electrode, which is configured to make electrical contact with the tissue.

In some embodiments, the joint includes a resilient member, which is configured to deform in response to pressure exerted on the distal tip when the distal tip engages the tissue. The resilient member may include a tubular piece of an elastic material having a helical cut therethrough along a portion of a length of the piece.

There is also provided, in accordance with an embodiment of the present invention, apparatus for performing a medical procedure on a body of a patient. The apparatus includes a probe, which includes an insertion tube, having a longitudinal axis and having a distal end; a distal tip, which is disposed at the distal end of the insertion tube and is configured to be brought into contact with tissue of the body; a joint, which couples the distal tip to the distal end of the insertion tube; and a joint sensor, contained within the probe, for sensing a position of the distal tip relative to the distal end of the insertion tube, the joint sensor including first and second subassemblies, which are disposed within the probe on opposite, respective sides of the joint and each include one or more magnetic transducers. A processor is coupled to apply a current to one of the first and second subassemblies, thereby causing the one of the subassemblies to generate at least one magnetic field, and is coupled to receive and process one or more signals output by the other of the first and second subassemblies responsively to the at least one magnetic field so as to detect changes in a position of the distal tip relative to the distal end of the insertion tube.

In some embodiments, the apparatus includes a magnetic field generator, for generating a further magnetic field in a vicinity of the body, and a position sensor in the probe for generating a position signal in response to the further magnetic field, wherein the processor is coupled to receive and process the position signal in order to compute coordinates of the probe relative to a frame of reference that is separate from the probe. In a disclosed embodiment, the position sensor includes at least one of the magnetic transducers in one of the first and second subassemblies.

There is additionally provided, in accordance with an embodiment of the present invention, apparatus for sensing movement of a joint in an assembly having a longitudinal axis passing through the joint. The apparatus includes first and second sensing subassemblies, which are disposed within the assembly on opposite, respective sides of the joint and each include one or more magnetic transducers. A processor is coupled to apply a current to one of the first and second assemblies, thereby causing the one of the assemblies to generate at least one magnetic field, and is coupled to receive and process one or more signals output by the other of the first and second assemblies responsively to the at least one magnetic field so as to detect changes in a disposition of the joint.

There is further provided, in accordance with an embodiment of the present invention, a method for performing a medical procedure on tissue in a body of a patient. The method includes applying to the body a probe, which includes an insertion tube and a distal tip, which is coupled to a distal end of the insertion tube by a joint, and which includes a joint sensor, which is contained within the probe and includes first and second subassemblies, which are disposed within the probe on opposite, respective sides of the joint and each include one or more magnetic transducers. The probe is advanced so that the distal tip engages and applies a pressure against the tissue, so as to cause a change in a position of the distal tip relative to the distal end of the insertion tube. A current is applied to one of the first and second subassemblies, thereby causing the one of the subassemblies to generate at least one magnetic field. One or more signals output are received by the other of the first and second subassemblies responsively to the at least one magnetic field and are processed so as to detect the change in the position of the distal tip.

In one embodiment, advancing the probe includes bringing an electrode on the distal tip into electrical contact with the tissue. The method may include applying electrical energy to the electrode so as to ablate a region of the tissue that is engaged by the distal tip, wherein the position of the distal tip relative to the distal end of the insertion tube changes in response to a pressure of the distal tip against the tissue, and wherein applying the electrical energy includes controlling application of the energy responsively to the pressure, as indicated by the position of the distal tip, so that the electrical energy is applied to the electrode when the pressure is within a desired range.

The present invention will be more fully understood from the following detailed description of the embodiments thereof, taken together with the drawings in which:

DETAILED DESCRIPTION OF THE INVENTION

The above-mentioned U.S. patent application Ser. No. 11/868,733 describes a catheter whose distal tip is coupled to the distal end of the catheter insertion tube by a spring-loaded joint, which deforms in response to pressure exerted on the distal tip when it engages tissue. A magnetic position sensing assembly within the probe, comprising coils on opposite sides of the joint, senses the position of the distal tip relative to the distal end of the insertion tube. Changes in this relative position are indicative of deformation of the spring and thus give an indication of the pressure.

Embodiments of the present invention that are described hereinbelow provide a new design of the sensing assembly, which facilitates more precise measurement of tip movement. The configuration of the coils in this new design permits precise sensing of very small deflections and compressions of the joint connecting the catheter tip to the insertion tube. Therefore, the pressure on the tip can be measured with enhanced accuracy, permitting the use a relatively stiffer spring in the catheter, which makes the catheter more reliable and easier to maneuver in the body.

Figure 1:
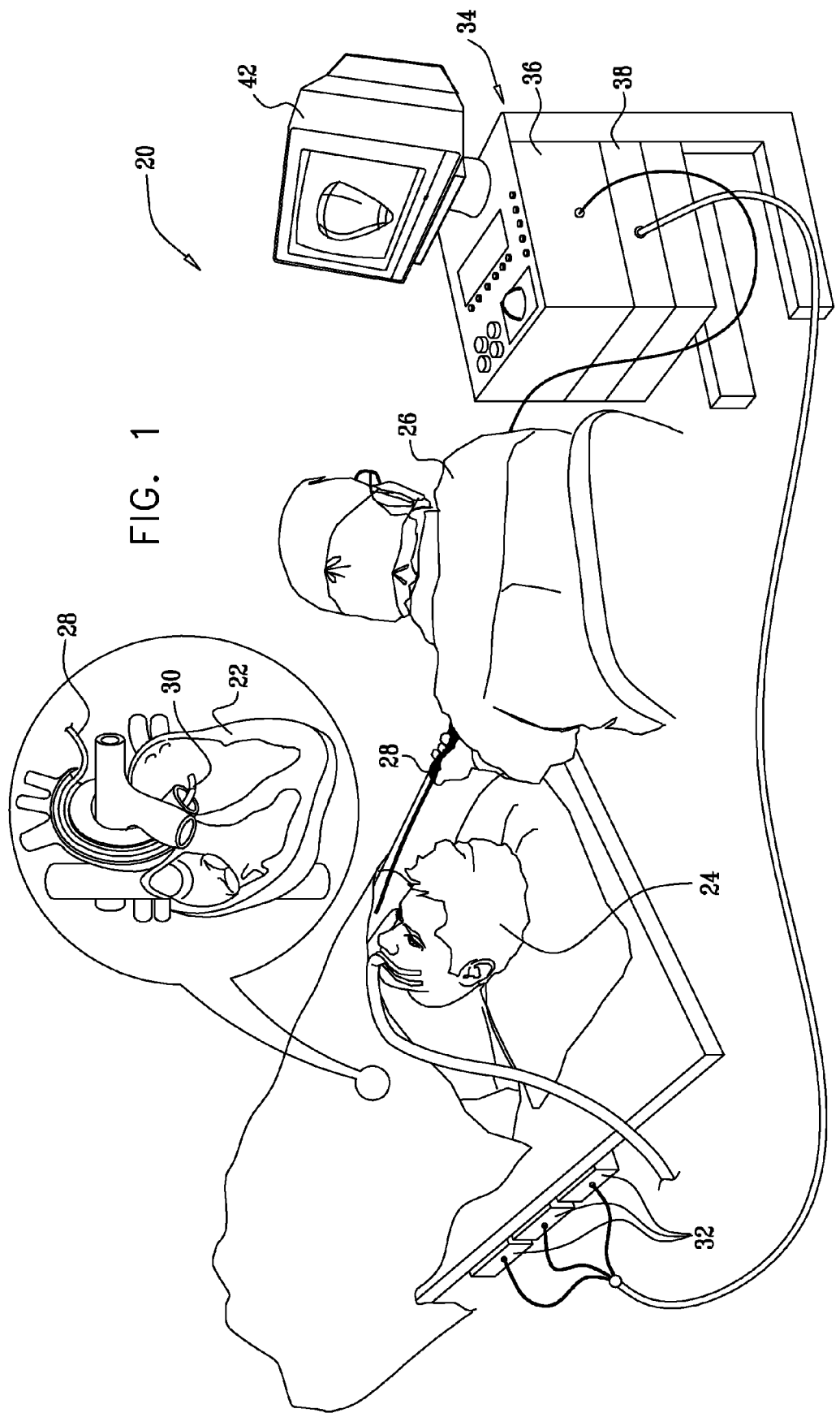
FIG. 1 is a schematic, pictorial illustration of a catheter-based medical system, in accordance with an embodiment of the present invention.

FIG. 1 is a schematic, pictorial illustration of a system 20 for cardiac catheterization, in accordance with an embodiment of the present invention. System 20 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used, mutatis mutandis, for other therapeutic and/or diagnostic purposes in the heart or in other body organs.

An operator 26, such as a cardiologist, inserts catheter 28 through the vascular system of a patient 24 so that a distal end 30 of the catheter enters a chamber of the patient's heart 22. The operator advances the catheter so that the distal tip of the catheter engages endocardial tissue at a desired location or locations. Catheter 28 is typically connected by a suitable connector at its proximal end to console 34. The console may comprise a radio frequency (RF) generator, which supplies high-frequency electrical energy via the catheter for ablating tissue in the heart at the locations engaged by the distal tip. Alternatively or additionally, the catheter and system may be configured to perform other therapeutic and diagnostic procedures that are known in the art.

Console 34 uses magnetic position sensing to determine position coordinates of distal end 30 of catheter 28 inside heart 22. For this purpose, a driver circuit 38 in console 34 drives field generators 32 to generate magnetic fields in the vicinity of the body of patient 24. Typically, the field generators comprise coils, which are placed below the patient's torso at known positions external to the patient. These coils generate magnetic fields within the body in a predefined working volume that contains heart 22. A magnetic field sensor within distal end 30 of catheter 28 (shown in FIG. 3) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618, 612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor may be carried out by dedicated or programmable digital hardware components. Based on the signals received from the catheter and other components of system 20, processor 36 drives a display 42 to give operator 26 visual feedback regarding the position of distal end 30 in the patient's body, as well as regarding displacement of the distal tip of the catheter, and status information and guidance regarding the procedure that is in progress.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end, as explained further hereinbelow.

Figure 2:
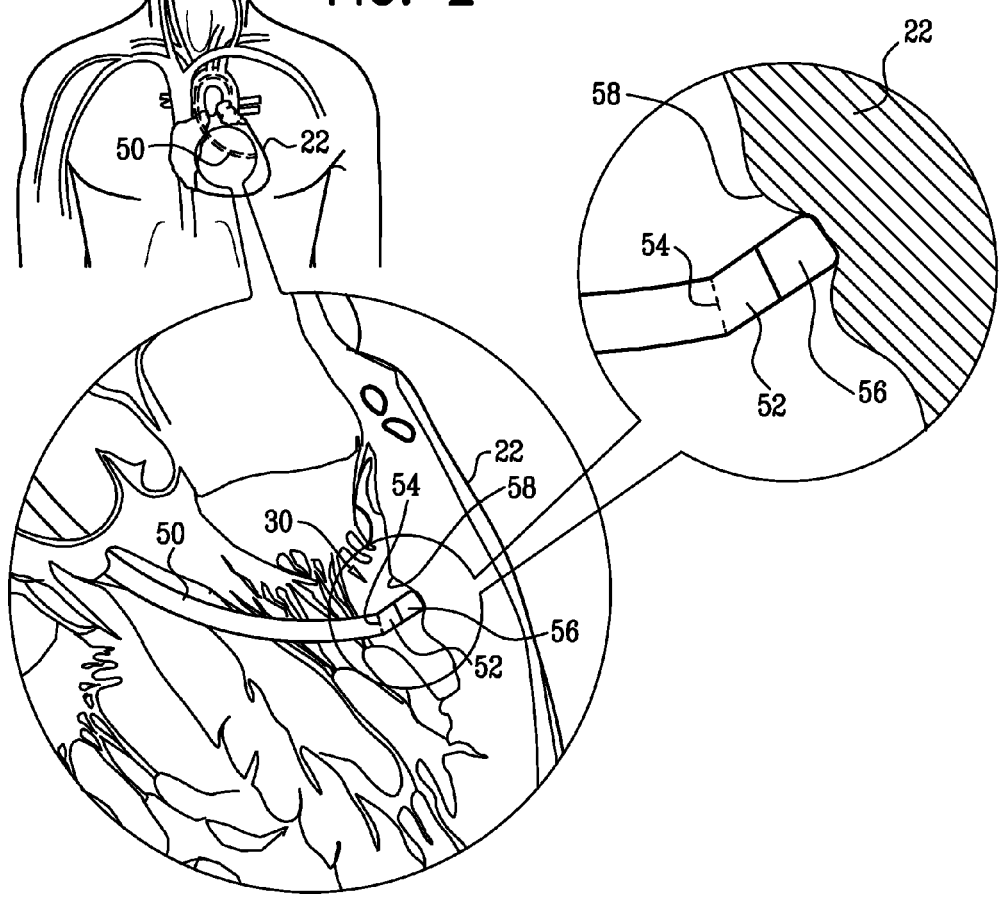
FIG. 2 is a schematic detail view showing the distal tip of a catheter in contact with endocardial tissue, in accordance with an embodiment of the present invention.

FIG. 2 is a schematic sectional view of a chamber of a heart 22, showing distal end 30 of catheter 28 inside the heart, in accordance with an embodiment of the present invention. The catheter comprises an insertion tube 50, which is typically inserted into the heart percutaneously through a blood vessel, such as the vena cava or the aorta. An electrode 56 on a distal tip 52 of the catheter engages endocardial tissue 58. Pressure exerted by the distal tip against the endocardium deforms the endocardial tissue locally, so that electrode 56 contacts the tissue over a relatively large area. In the pictured example, the electrode engages the endocardium at an angle, rather than head-on. Distal tip 52 therefore bends at an elastic joint 54 relative to the distal end of insertion tube 50 of the catheter. The bend facilitates optimal contact between the electrode and the endocardial tissue.

Because of the elastic quality of joint 54, the angle of bending and the axial displacement of the joint are proportional to the pressure exerted by tissue 58 on distal tip 52 (or equivalently, the pressure exerted by the distal tip on the tissue). Measurement of the bend angle and axial displacement thus gives an indication of this pressure. The pressure indication may be used by the operator of catheter 20 is ensuring that the distal tip is pressing against the endocardium firmly enough to give the desired therapeutic or diagnostic result, but not so hard as to cause undesired tissue damage.

Figure 3:
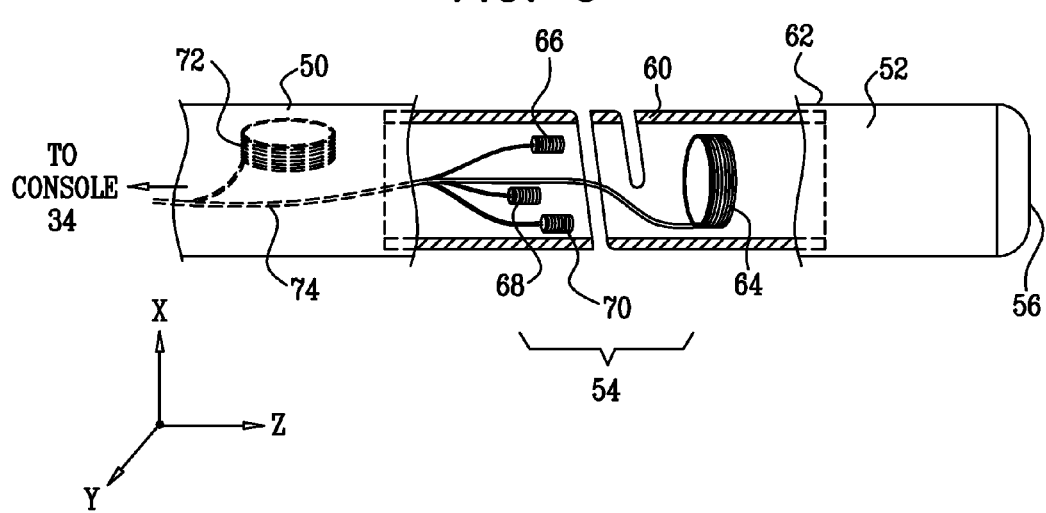
FIG. 3 is a schematic, sectional view showing details of the distal end of a catheter, in accordance with an embodiment of the present invention.

FIG. 3 is a schematic, sectional view of distal end 30 of catheter 28, showing details of the structure of the catheter in accordance with an embodiment of the present invention. Insertion tube 50 is connected to distal tip 52 by joint 54, as noted above. The insertion tube is covered by a flexible, insulating material 62, such as Celcon®, Teflon®, or heat-resistant polyurethane, for example. The area of joint 54 is covered, as well, by a flexible, insulating material, which may be the same as material 62 or may be specially adapted to permit unimpeded bending and compression of the joint. (This material is cut away in FIG. 3 in order to expose the internal structure of the catheter.) Distal tip 52 may be covered, at least in part, by electrode 56, which is typically made of a conductive material, such as a platinum/iridium alloy. Alternatively, other suitable materials may be used, as will be apparent to those skilled in the art. Further alternatively, for some applications, the distal tip may be made without a covering electrode. The distal tip is typically relatively rigid, by comparison with the flexible insertion tube.

Joint 54 comprises a resilient coupling member 60. In this embodiment, the coupling member has the form of a tubular piece of an elastic material, with a helical cut along a portion of its length. For example, the coupling member may comprise a superelastic alloy, such as nickel titanium (Nitinol). The helical cut causes the tubular piece to behave like a spring in response to forces exerted on distal tip 52. Further details regarding the fabrication and characteristics of this sort of coupling member are presented in U.S. patent application Ser. No. 12/134,592, filed Jun. 6, 2008, which is assigned to the assignee of the present patent application and whose disclosure is incorporated herein by reference. Alternatively, the coupling member may comprise a coil spring or any other suitable sort of resilient component with the desired flexibility and strength characteristics.

The stiffness of coupling member 60 determines the range of relative movement between tip 52 and insertion tube 50 in response to forces exerted on the distal tip. Such forces are encountered when the distal tip is pressed against the endocardium during an ablation procedure. The desired pressure for good electrical contact between the distal tip and the endocardium during ablation is on the order of 20-30 grams. The coupling member is configured to permit axial displacement (i.e., lateral movement along the axis of catheter 28) and angular deflection of the distal tip in proportion to the pressure on the tip. Measurement of the displacement and deflection by processor 36 gives an indication of the pressure and thus helps to ensure that the correct pressure is applied during ablation.

A joint sensing assembly, comprising coils 64, 66, 68 and 70 within catheter 28, provides accurate reading of the position of distal tip 52 relative to the distal end of insertion tube 50, including axial displacement and angular deflection. These coils are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in catheter 28 are divided between two subassemblies on opposite sides of joint 54: One subassembly comprises coil 64, which is driven by a current via a cable 74 from console 34 to generate a magnetic field. This field is received by a second subassembly, comprising coils 66, 68 and 70, which are located in a section of the catheter that is spaced axially apart from coil 64. (The term "axial," as used in the context of the present patent application and in the claims, refers to the direction of the longitudinal axis of distal end 30 of catheter 28, which is identified as the Z-direction in FIG. 3. An axial plane is a plane perpendicular to this longitudinal axis, and an axial section is a portion of the catheter contained between two axial planes.) Coils 66, 68 and 70 emit electrical signals in response to the magnetic field generated by coil 64. These signals are conveyed by cable 74 to processor 36, which processes the signals in order to measure the axial displacement and angular deflection of joint 54.

Coils 66, 68 and 70 are fixed in catheter 28 at different radial locations. (The term "radial" refers to coordinates relative to the catheter axis, i.e., coordinates in an X-Y plane in FIG. 3.) Specifically, in this embodiment, coils 66, 68 and 70 are all located in the same axial plane at different azimuthal angles about the catheter axis. For example, the three coils may be spaced azimuthally 120° apart at the same radial distance from the axis.

The axes of coils 64, 66, 68 and 70 are parallel to the catheter axis (and thus to one another, as long as joint 54 is undeflected). Consequently, coils 66, 68 and 70 will output strong signals in response to the field generated by coil 64, and the signals will vary strongly with the distances of coils 66, 68 and 70 from coil 64. (Alternatively, the axis of coil 64 and/or coils 66, 68 and 70 may be angled relative to the catheter axis, as long as the coil axes have a sufficient parallel component in order to give substantial signals.) Angular deflection of tip 52 will give rise to a differential change in the signals output by coils 66, 68 and 70, depending on the direction and magnitude of deflection, since one or two of these coils will move relatively closer to coil 64. Compressive displacement of the tip will give rise to an increase in the signals from all of coils 66, 68 and 70.

Processor 36 analyzes the signals output by coils 66, 68 and 70 in order to measure the deflection and displacement of joint 54. The sum of the changes in the signals gives a measure of the compression, while the difference of the changes gives the deflection. The vector direction of the difference gives an indication of the bend direction. A suitable calibration procedure may be used to measure the precise dependence of the signals on deflection and displacement of the joint.

Various other configurations of the coils in the sensing subassemblies may also be used, in addition to the configuration shown and described above. For example, the positions of the subassemblies may be reversed, so that that field generator coil is on the proximal side of joint 54, and the sensor coils are in the distal tip. As another alternative, coils 66, 68 and 70 may be driven as field generators (using time- and/or frequency-multiplexing to distinguish the fields), while coil 64 serves as the sensor. The sizes and numbers of the coils in FIG. 3 are shown only by way of example, and larger or smaller numbers of coils may similarly be used, in various different positions, so long as one of the subassemblies comprises at least two coils, in different radial positions, to allow differential measurement of joint deflection.

Prior calibration of the relation between pressure on tip 52 and movement of joint 54 may be used by processor 36 in translating the coil signals into terms of pressure. By virtue of the combined sensing of displacement and deflection, this pressure sensing system reads the pressure correctly regardless of whether the electrode engages the endocardium head-on or at an angle. The pressure reading is insensitive to temperature variations and free of drift, unlike piezoelectric sensors, for example. Because of the high sensitivity to joint motion that is afforded by the arrangement of coils 64, 66, 68 and 70 that is shown in FIG. 3, processor 36 can measure small displacements and deflections with high precision. Therefore, coupling member 60 can be made relatively stiff, and processor 36 will still be able to sense and measure accurately the pressure on tip 52. The stiffness of the coupling member makes it easier for the operator to maneuver and control the catheter.

One or more of coils 64, 66, 68 and 70 may also be used to output signals in response to the magnetic fields generated by field generators 32, and thus serve as position sensing coils. Processor 36 processes these signals in order to determine the coordinates (position and orientation) of distal end 30 in the external frame of reference that is defined by the field generators. Additionally or alternatively, one or more further coils 72 (or other magnetic sensors) may be deployed in the distal end of the catheter for this purpose. The position sensing coils in distal end 30 of catheter 28 enable console 34 to output both the location and orientation of the catheter in the body and the displacement and deflection of tip 52, as well as the pressure on the tip.

Although the operation of a magnetic position sensing assembly and its use in sensing pressure are described above in the context of catheter-based ablation, the principles of the present invention may similarly be applied in other applications that require accurate sensing of the movement of a joint, and particularly in therapeutic and diagnostic applications that use invasive probes, both in the heart and in other organs of the body. As one example, the devices and techniques for position and pressure sensing that are implemented in system 20 may be applied, mutatis mutandis, in guiding and controlling the use of a catheter insertion sheath. If the position of the sheath is not properly controlled and excessive force is used in its insertion, the sheath may perforate the heart wall or vascular tissue. This eventuality can be avoided by sensing the position of and pressure on the distal tip of the sheath. In this regard, the term "distal tip" as used herein should be understood to include any sort of structure at the distal end of a probe that may be bent and/or displaced relative to the main body of the probe.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:
1. A medical probe, comprising:
an insertion tube, having a longitudinal axis and having a distal end;
a distal tip, which is disposed at the distal end of the insertion tube and is configured to be brought into contact with a body tissue;
a joint, which couples the distal tip to the distal end of the insertion tube; and
a joint sensor, contained within the probe, for sensing a position of the distal tip relative to the distal end of the insertion tube, the joint sensor comprising first and second subassemblies, which are disposed within the probe on opposite, respective sides of the joint and each comprise one or more magnetic transducers, the joint sensor being configured to generate a signal indicative of an axial displacement and an orientation of the distal tip relative to the distal end of the insertion tube, wherein one of the first and second subassemblies is coupled to be driven by an electrical current to emit at least one magnetic field, and the other of the first and second subassemblies is coupled to output one or more signals in response to the at least one magnetic field, and wherein the signals are indicative of the position of the distal tip relative to the distal end of the insertion tube.

2. The probe according to claim 1, wherein the magnetic transducers comprises coils, and wherein the first subassembly comprises a first coil having a first coil axis parallel to the longitudinal axis of the insertion tube, and wherein the second subassembly comprises two or more second coils in different, respective radial locations within a section of the probe that is spaced apart axially from the first subassembly.

3. The probe according to claim 2, wherein the second coils have respective second coil axes that are parallel to the longitudinal axis of the insertion tube.

4. The probe according to claim 2, wherein the two or more second coils comprise at least three second coils.

5. The probe according to claim 4, wherein the at least three second coils are disposed within an axial plane of the probe at different, respective azimuthal angles about the longitudinal axis.

6. The probe according to claim 1, and comprising a position sensor for sensing position coordinates of the probe relative to a frame of reference that is separate from the probe.

7. The probe according to claim 1, wherein the distal tip comprises an electrode, which is configured to make electrical contact with the tissue.

8. The probe according to claim 1, wherein the joint comprises a resilient member, which is configured to deform in response to pressure exerted on the distal tip when the distal tip engages the tissue.

9. The probe according to claim 8, wherein the resilient member comprises a tubular piece of an elastic material having a helical cut therethrough along a portion of a length of the piece.

10. Apparatus for performing a medical procedure on a body of a patient, the apparatus comprising:
 a probe, which comprises:
  an insertion tube, having a longitudinal axis and having a distal end;
  a distal tip, which is disposed at the distal end of the insertion tube and is configured to be brought into contact with tissue of the body;
  a joint, which couples the distal tip to the distal end of the insertion tube; and
  a joint sensor, contained within the probe, for sensing a position of the distal tip relative to the distal end of the insertion tube, the joint sensor comprising first and second subassemblies, which are disposed within the probe on opposite, respective sides of the joint and each comprise one or more magnetic transducers; and
 a processor, which is coupled to apply a current to one of the first and second subassemblies, thereby causing the one of the subassemblies to generate at least one magnetic field, and which is coupled to receive and process one or more signals output by the other of the first and second subassemblies responsively to the at least one magnetic field so as to detect changes in a position of the distal tip relative to the distal end of the insertion tube.

11. The apparatus according to claim 10, wherein the magnetic transducers comprise coils, and wherein the first subassembly comprises a first coil having a first coil axis parallel to the longitudinal axis of the insertion tube, and wherein the second subassembly comprises two or more second coils in different, respective radial locations within a section of the probe that is spaced apart axially from the first subassembly.

12. The apparatus according to claim 10, wherein the changes in the position of the distal tip detected by the processor comprise an axial displacement of the distal tip and a deflection of the distal tip relative to the distal end of the insertion tube.

13. The apparatus according to claim 10, wherein the joint comprises a resilient member, which is configured to deform in response to pressure exerted on the distal tip when the distal tip engages the tissue.

14. The apparatus according to claim 13, wherein the processor is configured to generate, responsively to the detected changes in the position, an output that is indicative of the pressure exerted on the distal tip.

15. The apparatus according to claim 10, and comprising a magnetic field generator, for generating a further magnetic field in a vicinity of the body, and a position sensor in the probe for generating a position signal in response to the further magnetic field, wherein the processor is coupled to receive and process the position signal in order to compute coordinates of the probe relative to a frame of reference that is separate from the probe.

16. The apparatus according to claim 15, wherein the position sensor comprises at least one of the magnetic transducers in one of the first and second subassemblies.

17. Apparatus for sensing movement of a joint in an assembly having a longitudinal axis passing through the joint, the apparatus comprising:
 first and second sensing subassemblies, which are disposed within the assembly on opposite, respective sides of the joint and each comprise one or more magnetic transducers; and
 a processor, which is coupled to apply a current to one of the first and second assemblies, thereby causing the one of the assemblies to generate at least one magnetic field, and which is coupled to receive and process one or more signals output by the other of the first and second assemblies responsively to the at least one magnetic field so as to detect changes in a disposition of the joint.

18. The apparatus according to claim 17, wherein the magnetic transducers comprise coils, and wherein the first subassembly comprises a first coil having a first coil axis parallel to the longitudinal axis of the insertion tube, and wherein the second subassembly comprises two or more second coils in different, respective radial locations within a section of the assembly that is spaced apart axially from the first subassembly.

19. The apparatus according to claim 17, wherein the processor is configured to detect, by processing the one or more signals, an axial compression of the joint and an angular deflection of the joint.

20. The apparatus according to claim 17, wherein the joint comprises a resilient member, which is configured to deform in response to pressure exerted on the assembly, and wherein the processor is configured to generate, responsively to the detected changes in the disposition, an output that is indicative of the pressure exerted on the assembly.

21. A method for performing a medical procedure on tissue in a body of a patient, the method comprising:
 applying to the body a probe, which comprises an insertion tube and a distal tip, which is coupled to a distal end of the insertion tube by a joint, and which comprises a joint sensor, which is contained within the probe and comprises first and second subassemblies, which are disposed within the probe on opposite, respective sides of the joint and each comprise one or more magnetic transducers;
 advancing the probe so that the distal tip engages and applies a pressure against the tissue, so as to cause a change in a position of the distal tip relative to the distal end of the insertion tube;

applying a current to one of the first and second subassemblies, thereby causing the one of the subassemblies to generate at least one magnetic field; and receiving and processing one or more signals output by the other of the first and second subassemblies responsively to the at least one magnetic field so as to detect the change in the position of the distal tip.

22. The method according to claim 21, wherein the magnetic transducers comprise coils, and wherein the first subassembly comprises a first coil having a first coil axis parallel to a longitudinal axis of the insertion tube, and wherein the second subassembly comprises two or more second coils in different, respective radial locations within a section of the probe that is spaced apart axially from the first subassembly.

23. The method according to claim 21, wherein processing the one or more signals comprises detecting an axial displacement and an orientation of the distal tip relative to the distal end of the insertion tube.

24. The method according to claim 21, wherein the joint comprises a resilient member, which is configured to deform in response to the pressure on the distal tip, and wherein processing the one or more signals comprises generating, responsively to the detected change in the position, an indication of the pressure exerted on the distal tip.

25. The method according to claim 21, and comprising generating a further magnetic field in a vicinity of the body, and sensing a position signal output by one of the first and second subassemblies in response to the further magnetic field in order to compute coordinates of the probe relative to a frame of reference that is separate from the probe.

26. The method according to claim 21, wherein advancing the probe comprises bringing an electrode on the distal tip into electrical contact with the tissue.

27. The method according to claim 26, and comprising applying electrical energy to the electrode so as to ablate a region of the tissue that is engaged by the distal tip.

28. The method according to claim 27, wherein the position of the distal tip relative to the distal end of the insertion tube changes in response to a pressure of the distal tip against the tissue, and wherein applying the electrical energy comprises controlling application of the energy responsively to the pressure, as indicated by the position of the distal tip, so that the electrical energy is applied to the electrode when the pressure is within a desired range.

\* \* \* \* \*